United States Patent
Li et al.

(10) Patent No.: US 8,433,112 B2
(45) Date of Patent: Apr. 30, 2013

(54) METHOD AND APPARATUS FOR PROCESSING CHEST X-RAY IMAGES

(75) Inventors: Huanzhong Li, Beijing (CN); Dejun Wang, Beijing (CN); Mei Lin, Beijing (CN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 600 days.

(21) Appl. No.: 12/365,822

(22) Filed: Feb. 4, 2009

(65) Prior Publication Data

US 2009/0196481 A1  Aug. 6, 2009

(30) Foreign Application Priority Data

Feb. 5, 2008  (CN) .......................... 2008 1 0005497

(51) Int. Cl.
*G06K 9/00* (2006.01)
(52) U.S. Cl.
USPC .......................................... 382/128; 382/132
(58) Field of Classification Search .................. 382/128, 382/132
See application file for complete search history.

(56) References Cited

U.S. PATENT DOCUMENTS

| 3,869,602 | A  | * | 3/1975  | Sezaki et al. ............ 600/481 |
| 5,740,269 | A  | * | 4/1998  | Oh et al. .................. 382/133 |
| 5,825,936 | A  |   | 10/1998 | Clarke et al. |
| 5,862,249 | A  | * | 1/1999  | Jang et al. ................ 382/132 |
| 6,594,378 | B1 |   | 7/2003  | Li et al. |
| 7,221,787 | B2 |   | 5/2007  | Luo et al. |
| 7,251,353 | B2 | * | 7/2007  | Doi et al. ................. 382/128 |
| 7,274,810 | B2 |   | 9/2007  | Reeves et al. |
| 7,289,653 | B2 |   | 10/2007 | Zhang et al. |
| 7,295,870 | B2 |   | 11/2007 | Allain et al. |
| 7,315,635 | B2 | * | 1/2008  | Oosawa .................... 382/128 |
| 2002/0094119 | A1 | * | 7/2002 | Sahadevan ............. 382/132 |
| 2002/0097901 | A1 | * | 7/2002 | Xu et al. ................. 382/131 |
| 2003/0190067 | A1 | * | 10/2003 | Tsujii ..................... 382/132 |
| 2003/0215119 | A1 | * | 11/2003 | Uppaluri et al. ......... 382/128 |
| 2005/0147285 | A1 | * | 7/2005  | Tago et al. .............. 382/130 |
| 2005/0265606 | A1 | * | 12/2005 | Nakamura ............... 382/218 |

FOREIGN PATENT DOCUMENTS

JP  07-194583  8/1995

\* cited by examiner

*Primary Examiner* — Thanh Luu
(74) *Attorney, Agent, or Firm* — Armstrong Teasdale LLP

(57) ABSTRACT

A method for processing each of chest X-ray images photographed by an X-ray imaging apparatus, includes the steps of: analyzing characteristics of lung images in the chest X-ray images; sorting the chest X-ray images, based on said result of analysis; and displaying the result of sorting.

15 Claims, 10 Drawing Sheets

FIG. 2

| Patient Name | Patient ID | Accession# | Description | Date | Time | Phy | De-identify | a Stat |
|---|---|---|---|---|---|---|---|---|
| Anonymize... | 1159920... | 190347 | Radiografi... | 10/03/... | 18:13 | Ano | SMPTE | |
| Anonymize... | 1159913... | 171009 | Radiografi... | 10/03/... | 13:06 | Ano | Body exam auto scan | |
| Anonymize... | 1159913... | 170740 | Radiografi... | 10/03/... | 12:11 | Ano | PAC's Test images | |
| Anonymize... | 1159913... | 170704 | Radiografi... | 10/03/... | 12:13 | Ano | TG18 Samples | |
| Anonymize... | 1159913... | 170626 | Radiografi... | 10/03/... | 12:35 | Anonymized... | DX | |
| Anonymize... | 1159913... | 170618 | Radiografi... | 10/03/... | 13:04 | Anonymized... | DX | |
| Anonymize... | 1159912... | 165801 | Radiografi... | 10/03/... | 12:54 | Anonymized... | DX | |
| Anonymize... | 1159912... | 165718 | Radiografi... | 10/03/... | 16:02 | Anonymized... | DX | |
| CDRAD tes... | NEW ID... | | | 10/23/... | 10:35 | | DX | |
| chen jianguo | 27499 | | | 10/23/... | 10:25 | | DX | |
| Chest_Los | NEW ID... | | | 10/24/... | 10:27 | | DX | |

FIG. 3

METHOD AND APPARATUS FOR PROCESSING CHEST X-RAY IMAGES

CROSS REFERENCE TO RELATED APPLICATIONS

This application claims the benefit of Chinese Patent Application No. 200810005497.0 filed Feb. 5, 2008, which is hereby incorporated by reference in its entirety.

BACKGROUND OF THE INVENTION

The embodiments described herein relate to an image processing method and apparatus, and particularly to a method and apparatus for processing chest X-ray images photographed by an X-ray imaging apparatus.

As a type of X-ray imaging apparatus, there is known a Digital Radiography (DR) apparatus. Since each X-ray image photographed by the DR apparatus is suitable for digital image processing, it is practiced to obtain information useful in image reading and diagnosis through an image analyzing process (refer to, for example, Japanese Unexamined Patent Publication No. Hei 7(1995)-194583 (paragraph numbers 0011-0012 and FIG. 1)).

Since the number of target images is large when screening is done by chest X-ray images photographed by the DR apparatus, a large amount of doctor's labor is required for image reading and diagnosis. Therefore, there is a demand for execution of screening as efficient as possible. However, the image analyzing process has no effect on an efficiency improvement in screening.

It is desirable that the problem described previously is solved.

BRIEF DESCRIPTION OF THE INVENTION

In a first aspect, a method for processing each of chest X-ray images photographed by an X-ray imaging apparatus includes the steps of analyzing characteristics of lung images in the chest X-ray images, sorting the chest X-ray images, based on the result of analysis, and displaying the result of sorting.

In a second aspect, and according to the first aspect, wherein the characteristics include left-right symmetry of the lung images.

In a third aspect, and according to the first aspect, wherein the characteristics include characteristics of costophrenic angles.

In a fourth aspect, and according to the first aspect, wherein the characteristics include characteristics of pulmonary hila.

In a fifth aspect, and according to the fourth aspect, wherein the characteristics of the pulmonary hila include size characteristics of the pulmonary hila.

In a sixth aspect, and according to the fourth aspect, wherein the characteristics of the pulmonary hilum include a characteristic of intensity of each pulmonary-hilum image.

In a seventh aspect, and according to the first aspect, wherein the characteristics include continuity of ribs.

In an eighth aspect, and according to the first aspect, wherein the characteristics include a characteristic of a heart width.

In a ninth aspect, and according to the first aspect, wherein the characteristics include a characteristic of intensity of each lung image.

In a tenth aspect, and according to the ninth aspect, wherein the intensity includes an average intensity.

In an eleventh aspect, an image processing apparatus for processing chest X-ray images photographed by an X-ray imaging apparatus includes a device for analyzing characteristics of lung images in the chest X-ray images, a device for sorting the chest X-ray images, based on the result of analysis, and a device for displaying the result of sorting.

In a twelfth aspect, and according to the eleventh aspect, wherein the characteristics include left-right symmetry of the lung images.

In a thirteenth aspect, and according to the eleventh aspect, wherein the characteristics include characteristics of costophrenic angles.

In a fourteenth aspect, and according to the eleventh aspect, wherein the characteristics include characteristics of pulmonary hila.

In a fifteenth aspect, and according to the fourteenth aspect, wherein the characteristics of the pulmonary hila include size characteristics of the pulmonary hila.

In a sixteenth aspect, and according to the fourteenth aspect, wherein the characteristics of the pulmonary hilum include a characteristic of intensity of each pulmonary-hilum image.

In a seventeenth aspect, and according to the eleventh aspect, wherein the characteristics include continuity of ribs.

In an eighteenth aspect, and according to the eleventh aspect, wherein the characteristics include a characteristic of a heart width.

In a nineteenth aspect, and according to the eleventh aspect, wherein the characteristics include a characteristic of intensity of each lung image.

In a twentieth aspect, and according to the nineteenth aspect, wherein the intensity includes an average intensity.

According to the first aspect, a method for processing each of chest X-ray images photographed by an X-ray imaging apparatus analyzes characteristics of lung images in the chest X-ray images, sorts the chest X-ray images, based on the result of analysis, and displays the result of sorting. Therefore, an image processing method can be realized which is useful in an efficiency improvement in screening.

According to the eleventh aspect, an apparatus for processing chest X-ray images photographed by an X-ray imaging apparatus includes a device for analyzing characteristics of lung images in the chest X-ray images, a device for sorting the chest X-ray images, based on the result of analysis, and a device for displaying the result of sorting. It is therefore possible to realize an image processing apparatus useful in an efficiency improvement in screening.

According to the second or twelfth aspect, sorting based on whether left-right symmetry is good or bad can be carried out since the characteristics include left-right symmetry of lung images.

According to the third or thirteenth aspect, sorting based on the size of costophrenic angles can be performed since the characteristics include the characteristics of the costophrenic angles.

According to the fourth or fourteenth aspect, sorting based on whether pulmonary hila are good or bad can be conducted since the characteristics include the characteristics of the pulmonary hila.

According to the fifth or fifteenth aspect, sorting based on the size of the pulmonary hila can be conducted since the characteristics of the pulmonary hila include size characteristics of the pulmonary hila.

According to the sixth or sixteenth aspect, sorting based on the magnitude of intensity of each pulmonary hilum image can be done since the characteristics of the pulmonary hilum include a characteristic of intensity of each pulmonary hilum image.

According to the seventh or seventeenth aspect, sorting based on whether the continuity of ribs is good or bad can be conducted since the characteristics include the continuity of the ribs.

According to the eighth or eighteenth aspect, sorting based on the size of a heart width can be performed since the characteristics include the characteristic of the heart width.

According to the ninth or nineteenth aspect, sorting based on the magnitude of intensity of each lung image can be conducted since the characteristics include a characteristic of intensity of each lung image.

According to the tenth or twentieth aspect, sorting based on the magnitude of average intensity of each lung image can be conducted since the intensity includes an average intensity.

Further objects and advantages of the present invention will be apparent from the following description of the preferred embodiments of the invention as illustrated in the accompanying drawings.

BRIEF DESCRIPTION OF THE DRAWINGS

FIG. 2 is a diagram showing one example of a working screen for screening by a halftone photograph.

FIG. 3 is a diagram showing one example of a working screen for screening by a halftone photograph.

DETAILED DESCRIPTION OF THE INVENTION

Embodiments of the invention will be explained below with reference to the accompanying drawings. Incidentally, the invention is not limited to the embodiments described herein.

Figure 1:
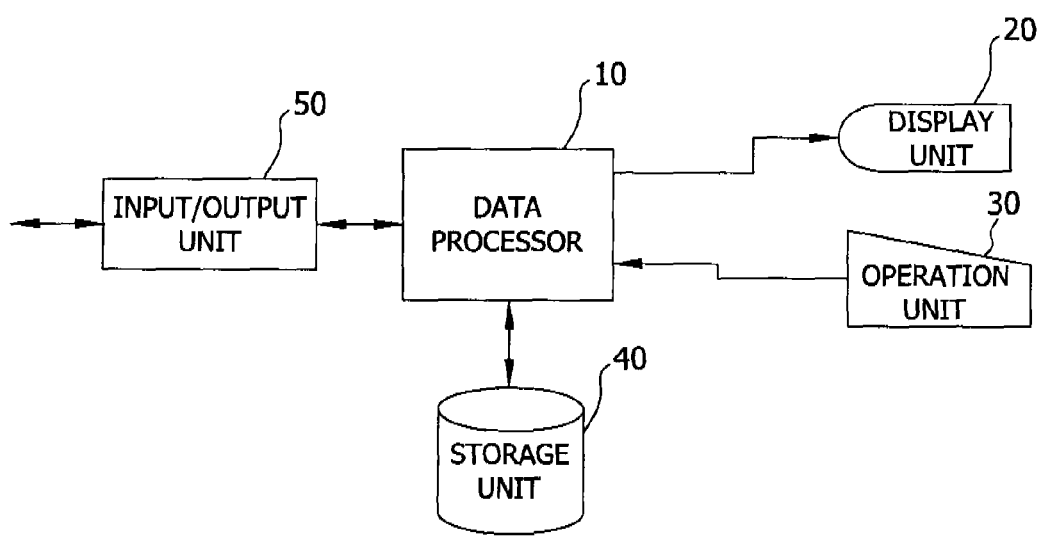
FIG. 1 is a block diagram showing a configuration of an exemplary image processing apparatus.

A configuration of an image processing apparatus is shown in FIG. 1 in a block diagram. The present apparatus is one example of the best mode for carrying out the invention. One example of the best mode for carrying out the invention related to the image processing apparatus is illustrated by the configuration of the present apparatus. One example of the best mode for carrying out the invention related to an image processing method is shown by the operation of the present apparatus.

As shown in FIG. 1, the present apparatus has a data processor 10, a display unit 20, an operation unit 30, a storage unit 40 and an input/output unit 50. The data processor 10 performs data processing to be described later, based on interactive operations by a user through the display unit 20 and the operation unit 30.

The data processor 10 also performs the input/output of data to/from an external device through the input/output unit 50. Each chest X-ray image for screening is inputted from the external device through the input/output unit 50 and stored in the storage unit 40. The external device is for example, a DR apparatus, a medical image server or the like. Incidentally, the present apparatus may be part of the DR apparatus or the medical image server. In such a case, it is always unnecessary to provide the input/output unit 50.

As will be described in detail later, the present apparatus analyzes the characteristics of lung images in the chest X-ray images, sorts the chest X-ray images, based on the result of analysis and display the result of sorting. The displayed result of sorting is used by a user as screening support information.

One example of a working screen used by the user is shown in FIG. 2. The working screen is displayed on the display unit 20. As shown in FIG. 2, an image list target for screening is displayed on the working screen.

Display items on the image list are a Patient Name, an ID (Patient ID), an Accession #, Description, Date, etc. The image list can be scrolled up and down.

A menu bar located above the screen includes a pull down menu. A Body exam auto scan is included in the pull down menu. The Body exam auto scan is called simply "auto scan" below.

When the user selects the auto scan, the present apparatus executes the auto scan on all images in the image list. The auto scan is a process for analyzing the characteristics of lung images with respect to chest X-ray images, sorting the chest X-ray images, based on the result of analysis and displaying the result of sorting.

Figure 3:
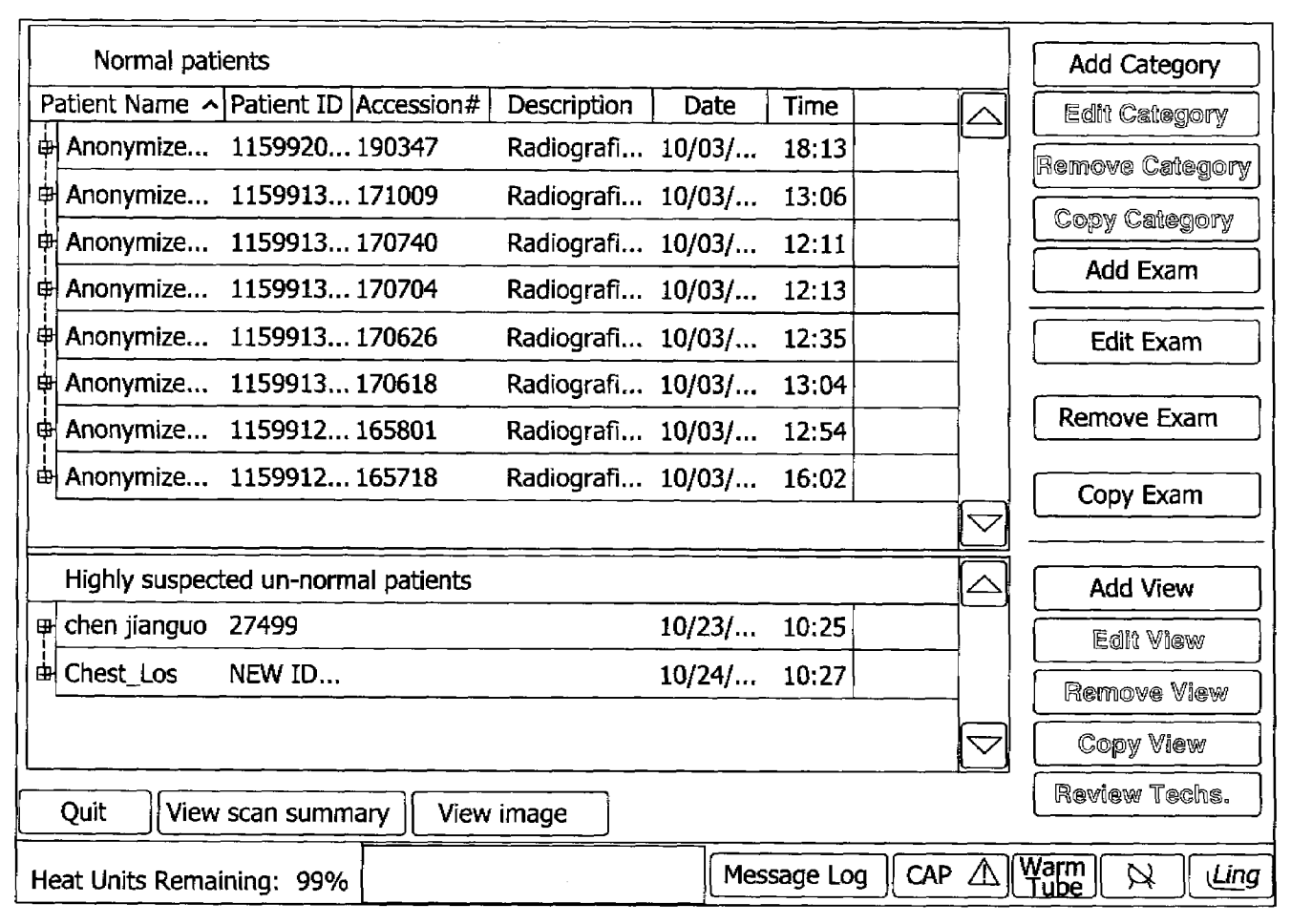

One example of a display screen indicative of the result of auto scan is shown in FIG. 3. As shown in FIG. 3, image lists are respectively displayed on the upper half of the screen and the lower half thereof. The upper half indicates the image list of normal patients, and the lower half indicates the image list of highly suspected un-normal patients.

That is, as the result of auto scan, targets for screening are displayed with being divided into a normal group and a highly suspected un-normal group. Therefore, the user performs image reading and diagnosing on the highly suspected un-normal group preferentially and thereby can carry out the screening efficiently.

Figure 4:
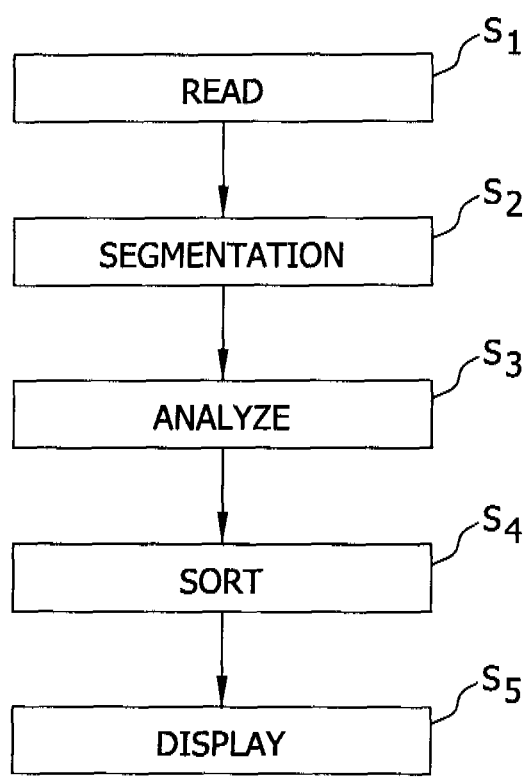
FIG. 4 is a flow chart of image processing.

The operation of the present apparatus is shown in FIG. 4 by a flow chart. As shown in FIG. 4, the operation of the present apparatus is performed in accordance with five steps S1, S2, S3, S4 and S5. Step S1 is a read step. Step S2 is a segmentation step. Step S3 is an analysis step. Step S4 is a sorting step. Step S5 is a display step. These steps are executed by the data processor 10.

Figure 5:
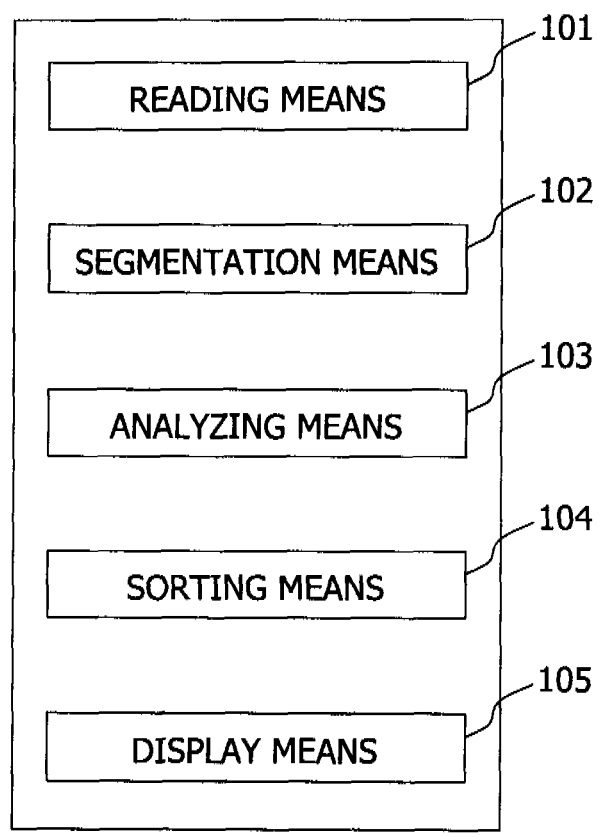
FIG. 5 is a block diagram showing a configuration of a data processor related to the image processing apparatus.

As shown in FIG. 5, the data processor 10 is provided with a reading device 101, a segmentation device 102, an analyzing device 103, a sorting device 104 and a display device 105 in association with the respective steps. Principal parts of these devices are programs or the like of the data processor 10. However, the input/output unit 50 is included in the reading device 101, and the display unit 20 is included in the display device 105.

The analyzing device 103 is one example of a device for analyzing the characteristics of lung images in each chest X-ray image. The sorting device 104 is one example of a device for sorting the chest X-ray images, based on the result of analysis in the invention. The display device 105 is one example of a device for displaying the result of sorting in the invention.

The operation of the present apparatus will be explained. At the read Step S1, each chest X-ray image is read. The reading of each chest X-ray image is performed by the reading device 101. The reading is performed on all chest X-ray images target for screening. The read chest X-ray images are stored in the storage unit 40.

Figure 6:
FIG. 6 is a diagram showing one example of a chest X-ray image by a halftone photograph.

One example of a chest X-ray image is shown in FIG. 6. The chest X-ray image is an antero-posterio (AP) penetration image. In the AP penetration image, the right side facing toward a patient indicates the left side of the patient, and the left side facing toward the patient indicates the right side of the patient. The chest X-ray image is also taken as a postero-anterio (PA) penetration image. In the PA penetration image, the right side facing toward the patient indicates the right side of the patient, and the left side facing toward the patient indicates the left side of the patient. For convenience of explanation, the lung located on the right side facing toward the patient is called right lung, and the lung located on the left side facing toward the patient is called left lung, regardless of either AP or PA.

At the segmentation Step S2, segmentation of each lung image is performed. The lung-image segmentation is performed on all chest X-ray images stored in the storage unit 40 by the segmentation device 102 one by one. The chest X-ray image is called simply "image" below.

Figure 7:
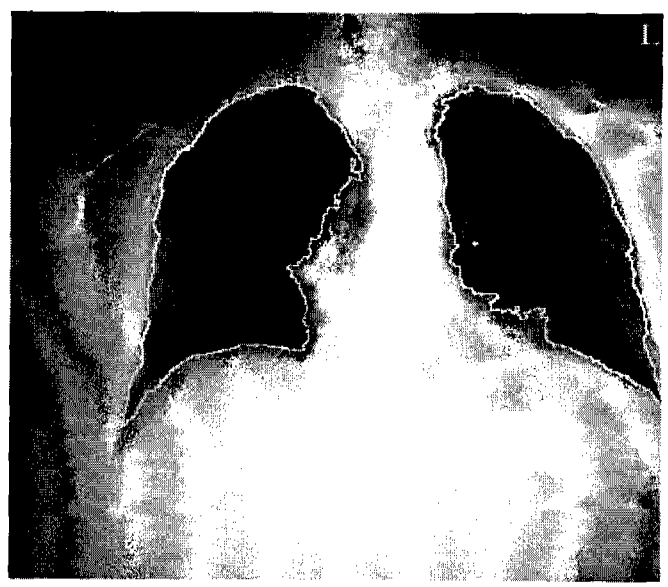
FIG. 7 is a diagram showing one example of segmentation of each lung image by a halftone photograph.

One example of the result of segmentation is shown in FIG. 7. As shown in FIG. 7, the contours of lung images are determined by segmentation. The segmentation is done using the known algorithm such as the active shape model, level sets, water shed, region growing, manford-shah, active contour model, expectation maximization, or the like.

At the analysis step S3, an analysis is conducted. The analysis is executed on the lung images subjected to the segmentation step by step by the analyzing device 103. The analysis is performed on the characteristics of the lung images. As the characteristics target for analysis, for example, six types of characteristics are adopted.

The six types of characteristics include, for example, the left-right symmetry of lung images, the characteristics of costophrenic angles, the characteristics of pulmonary hila, the continuity of ribs, the heart width characteristics, and the characteristic of the intensity of each lung image. Incidentally, the characteristics targets for analysis are not limited to these, but may be suitable characteristics. The number of characteristics may be either greater or smaller than the six types.

Figure 8:
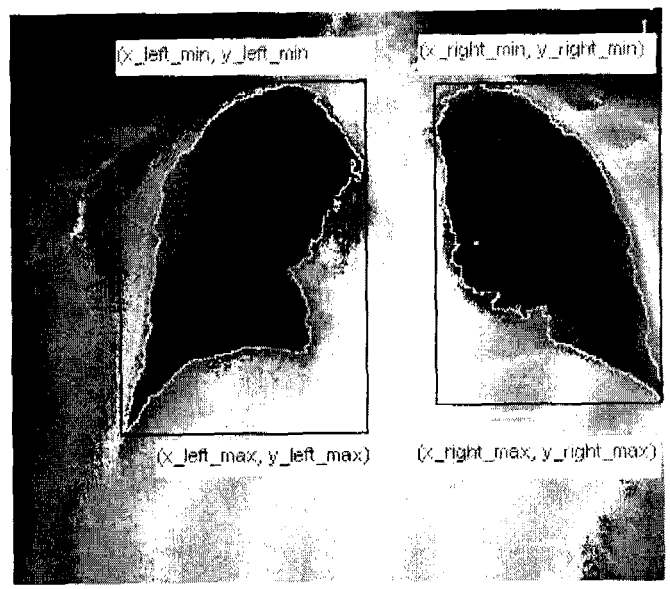
FIG. 8 is a diagram showing one example of an image in an analytical process by a halftone photograph.

One example of an analysis on the left-right symmetry of the lung images is shown in FIG. 8. As shown in FIG. 8, circumscribed rectangles are respectively determined with respect to the right and left lungs. The left-right symmetry of the lung images is decided based on the difference in size between the circumscribed rectangles.

The size of the circumscribed rectangle of the right lung is determined from xy coordinates of two vertices placed in a diagonal relationship, i.e., the following coordinates (X_right_min, Y_right_min) and (X_right_max, Y_right_max).

The size of the circumscribed rectangle of the left lung is determined from xy coordinates of two vertices placed in a diagonal relationship, i.e., the coordinates (X_left_min, Y_left_min) and (X_left_max, Y_left_max).

When the difference in size between the circumscribed rectangles of the left and right lungs is within a predetermined allowable range, it is determined that the left-right symmetry of the lungs exists. When the difference is not within the allowable range, it is determined that no left-right symmetry thereof exists.

At this time, a point 0 may be applied to an image in which the left-right symmetry of the lungs is determined to exist, and a point 1 may be applied to an image in which the left-right symmetry thereof is determined not to exist. Incidentally, the point may be a point greater than 1 or a point smaller than 1. The points may be made different every characteristic target for analysis without uniform assignment. This is taken in like manner below.

At the sorting step S4, the sorting of images is conducted. The sorting is conducted one by one based on the result of analysis on the left-right symmetry. Each image having the left-right symmetry is sorted into a normal group, and each image free of the left-right symmetry is sorted into a highly suspected un-normal group. Incidentally, when the points are applied to the images, the sorting step S4 may be conducted after the analysis of all remaining characteristics has been finished. This is taken similarly below.

Figure 9:
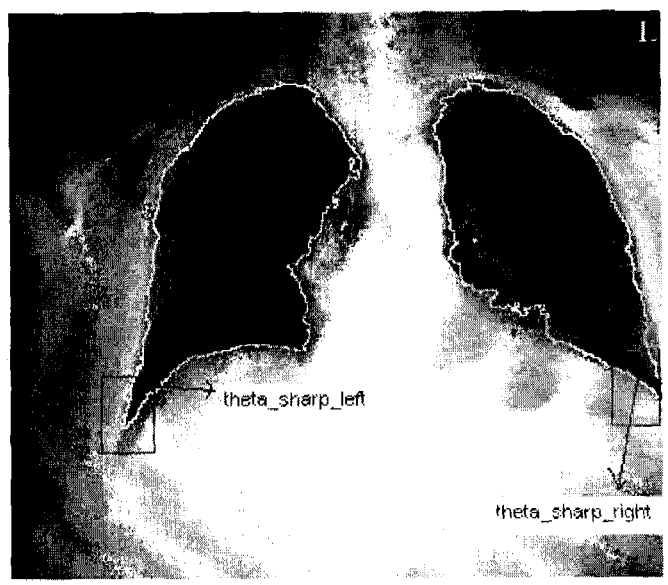
FIG. 9 is a diagram showing one example of an image in an analytical process by a halftone photograph.

One example of an analysis on the characteristics of the costophrenic angles is shown in FIG. 9. As shown in FIG. 9, the costophrenic angles, that is, the V-shaped open angles of lung-image contours lying within unillustrated rectangular regions are determined from the expressions theta_sharp_right and theta_sharp_left.

It is determined whether their costophrenic angles are smaller than the predetermined threshold value theta_threshold.

That is, it is determined whether theta_sharp_right<theta_threshold and/or whether theta_sharp_left<theta_threshold.

When the point is applied to each image, a point 0 is applied to images in which both of the costophrenic angles of the left and right lungs are smaller than the predetermined threshold value, whereas a point 1 is applied to each image in which either of the costophrenic angles of the left and right lungs is not smaller than the predetermined threshold value.

At the sorting step S4, the sorting of images is conducted. The sorting is conducted one by one based on the result of analysis on the costophrenic angles. Images in which both of the costophrenic angles of the left and right lungs are smaller than the predetermined threshold value are classified into a normal group, and each image in which either of the costophrenic angles of the left and right lungs is not smaller than the predetermined threshold value is classified into a highly suspected un-normal group.

Figure 10:
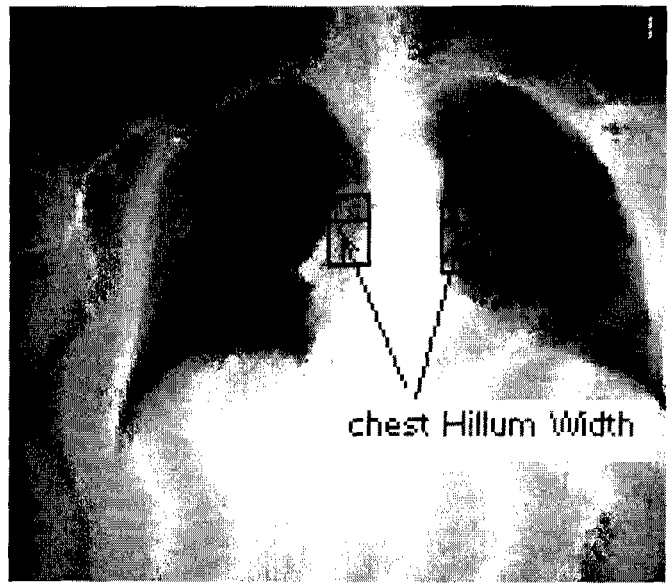
FIG. 10 is a diagram showing one example of an image in an analytical process by a halftone photograph.

One example of an analysis on the characteristics of the pulmonary hila is shown in FIG. 10. As shown in FIG. 10, pulmonary hila images are detected with respect to the right and left lungs, based on image's intensities, and their widths (lengths of linear portions indicated by arrows), i.e., the widths of the pulmonary hila are determined from the expressions chest_hillum_width_right and chest_hillum_width left.

It is determined whether the widths of the pulmonary hila are smaller than a predetermined threshold value chest_hillum_width_threshold.

That is, the following determining expressions are used it is determined whether chest_hillum_width_right<chest_hillum_width_threshold and/or whether chest_hillum_width_left<chest_hillum_width_threshold.

When the point is applied to each image, a point 0 is applied to images in which both of the widths of the pulmonary hila of the left and right lungs are smaller than the predetermined threshold value, whereas a point 1 is applied to images in which either of the widths of the pulmonary hila of the left and right lungs or both thereof are not smaller than the predetermined threshold value.

At the sorting step S4, the sorting of images is conducted. The sorting is conducted one by one based on the result of analysis on the widths of the pulmonary hila. Images in which both of the pulmonary-hilum widths of the left and right lungs are smaller than the predetermined threshold value are classified into a normal group, and images in which either of the pulmonary-hilum widths of the left and right lungs or both thereof are not smaller than the predetermined threshold value are classified into a highly suspected un-normal group.

As to the images of the pulmonary hila, the average or mean intensities of such rectangular region as shown in the drawing containing the images of the pulmonary hila are determined from the expressions chest_hillum_intensity_right and chest_hillum_intensity_left.

It is determined whether their average intensities are smaller than the predetermined threshold value chest_hillum_intensity_threshold.

That is, the following determining expressions are used it is determined whether chest_hillum_intensity_right<chest_hillum_intensity_threshold and/or whether chest_hillum_intensity_left<chest_hillum_intensity_threshold.

When the point is applied to each image, a point 0 is applied to images in which both of the average intensities of the left and right pulmonary hilum images are smaller than the predetermined threshold value, whereas a point 1 is applied to images in which either of the average intensities of the left and right pulmonary hilum images or both thereof are not smaller than the predetermined threshold value.

At the sorting step S4, the sorting of images is performed. The sorting is conducted one by one based on the result of analysis on the average intensities of the pulmonary hilum images. Images in which both of the average intensities of the left and right pulmonary-hilum images are smaller than the predetermined threshold value are classified into a normal group, and images in which either of the average intensities of the left and right pulmonary-hilum images or both thereof are not smaller than the predetermined threshold value are classified into a highly suspected un-normal group.

Figure 11:
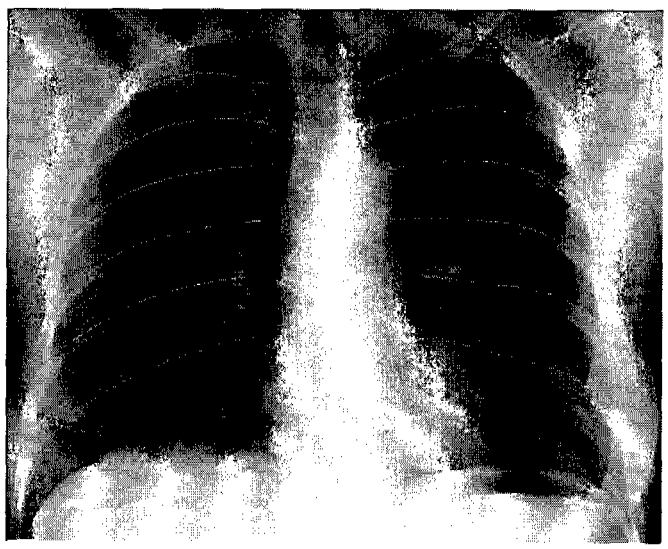
FIG. 11 is a diagram showing one example of an image in an analytical process by a halftone photograph.

One example of an analysis on the continuity of ribs is shown in FIG. 11. As shown in FIG. 11, the continuities of the ribs are respectively determined with respect to the right lung and the left lung. The continuities of the ribs are determined by searching the center lines of the ribs with respect to respective rib images.

The known algorithms such as the active shape model, manford-shah, Chan-Vese model, Baycsian classification, Wave-let genetic algorithm, etc. are used for the searching of the center lines of the rib images.

When the point is applied to each image, a point 0 is applied to images in which all the ribs are continuous at the left and right lungs, whereas a point 1 is applied to each image in which even one rib is discontinuous due to, for example, a rib fracture or the like at either of the left and right lungs.

At the sorting step S4, the sorting of images is done. The sorting is conducted one by one based on the result of analysis on the continuity of each rib. Images in which all the ribs are continuous at the left and right lungs are classified into a normal group. Each image in which even one rib is discontinuous at either one of the left and right lungs is classified into a highly suspected un-normal group.

Figure 12:
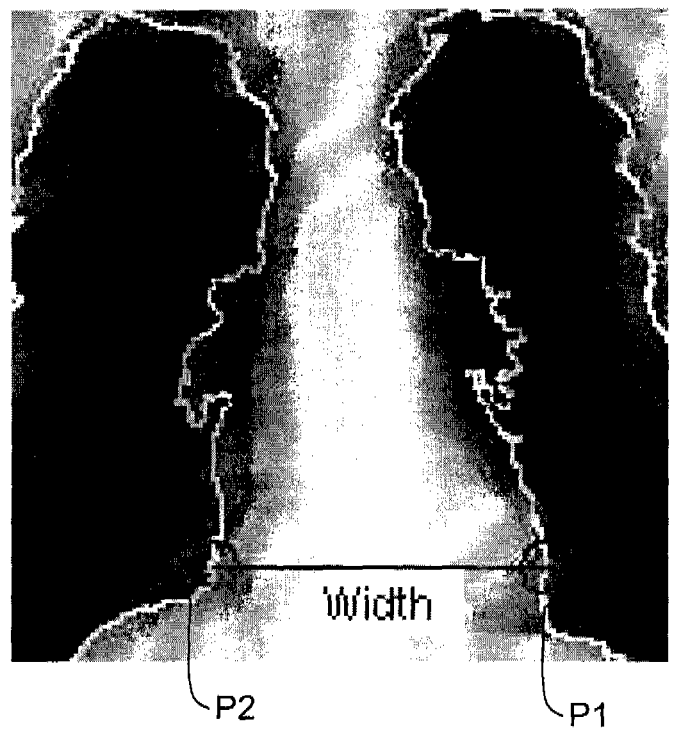
FIG. 12 is a diagram showing one example of an image in an analytical process by a halftone photograph.

One example of analysis on the heart width characteristics is shown in FIG. 12. As shown in FIG. 12, a heart width, i.e., the difference between x coordinates at a left lower end P1 of the right lung and a right lower end P2 of the left lung is determined from the expression heart_width.

It is determined whether the heart width falls between two predetermined threshold values heart_width_min and heart_width max.

That is, the following determining expressions are used it is determined whether heart_width_min<heart_width<heart_width_max.

Upon applying the point to each image, a point 0 is applied to each image in which the heart width is within a predetermined range, whereas a point 1 is applied to each image in which the heart width is beyond the predetermined range.

At the sorting step S4, the sorting of images is done. The sorting is conducted one by one based on the result of analysis on the heart width. Each image in which the heart width is within the predetermined range is sorted into a normal group, and each image in which the heart width is beyond the predetermined range, is sorted into a highly suspected un-normal group.

Figure 13:
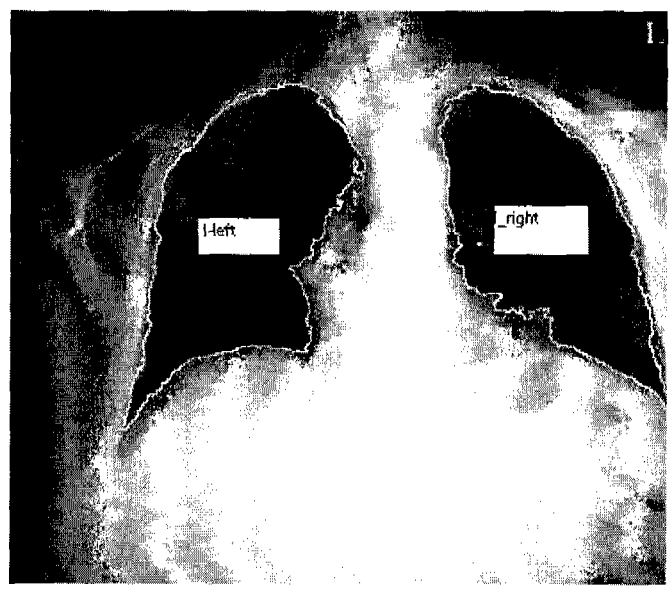
FIG. 13 is a diagram showing one example of an image in an analytical process by a halftone photograph.

One example of an analysis on the characteristics of intensities of lung images is shown in FIG. 13. As shown in FIG. 13, the average intensities in lung-image contours are determined with respect to the right lung and the left lung respectively as the expressions I_right and I_left.

It is determined whether those average intensities are smaller than the predetermined threshold value I-check_average_threshold.

That is, the following determining expressions are used it is determined whether I_right<I-check_average_threshold and/or whether I_left<I-check_average_threshold.

Upon applying the point to each image, a point 0 is applied to images in which both of the average intensities of the left and right lungs are not smaller than the predetermined threshold value, whereas a point 1 is applied to images in which either one of the average intensities of the left and right lungs or both thereof are smaller than the predetermined threshold value.

At the sorting step S4, the sorting of images is done. The sorting is performed one by one based on the result of analysis on the average intensities of the pulmonary hilum images. Images in which both of the average intensities of the left and right lungs are not smaller than the predetermined threshold value are classified into a normal group. Images in which either one of the average intensities of the left and right lungs or both thereof are smaller than the predetermined threshold value, are classified into a highly suspected un-normal group.

As to the intensity of each lung image, the lung images are divided into a high intensity area and a low intensity area by histogram segmentation, and the ratio in area between the whole region and the high intensity area is determined from the expression high_intensity_area/whole_lung_region.

It is determined whether this value is larger than a predetermined threshold value lung_high_threshold_ratio.

That is, the following determining expression is used it is determined whether high_intensity_area/whole_lung_region>lung_high_threshold_ratio.

Upon applying the point to the images, a point 0 is applied to each image in which the ratio in area between the whole region and the high intensity area is not larger than the predetermined threshold value, whereas a point 1 is applied to each image in which the ratio in area between the whole region and the high intensity area is larger than the predetermined threshold value.

Figure 14:
FIG. 14 is a diagram showing one example of a chest X-ray image by a halftone photograph.

At the sorting step S4, the sorting of images is done. The sorting is performed one by one based on the result of analysis on the intensities of the pulmonary hilum images. Each image in which the ratio in area between the whole region and the high intensity area is not larger than the predetermined threshold value is sorted into a normal group. Each image in which the ratio in area therebetween is larger than the predetermined threshold value is sorted into a highly suspected un-normal group. Thus, as shown in FIG. 14, for example, an image in which a high intensity area becomes large at the left lung due to lung cancer or the like, is reliably sorted into a highly suspected un-normal group.

A list of the images sorted according to the above-described image processing is displayed on such a working screen as shown in FIG. 3. The upper half of the screen is a list of images sorted into a normal group, and the lower half of the screen is a list of images sorted into a highly suspected un-normal group. Thus, the results of sorting are displayed as image lists set every group.

The sorting is not limited to the two types of normality and un-normality upon applying the points to the images. Points are added every image, and images may be ranked and displayed according to a total point. Thus, since the images are placed in a high rank as they become high in abnormality, image reading or the like made high in priority according to the rank is enabled.

The above-described functions may be incorporated into the DR apparatus. In this case, the auto scan is conducted each time chest X-ray images are photographed, and the result of photography can be displayed together with the chest X-ray images. Normality/un-normality or the degree of abnormality is recognized on the spot.

Many widely different embodiments of the invention may be configured without departing from the spirit and the scope of the present invention. It should be understood that the present invention is not limited to the specific embodiments described in the specification, except as defined in the appended claims.

What is claimed is:

1. A method for processing each of a plurality of chest X-ray images photographed by an X-ray imaging apparatus, said method comprising:
   analyzing at least one of size characteristics of pulmonary hila of lung images and a characteristic of intensity of each pulmonary-hilum image of lung images in the plurality of chest X-ray images;
   applying a point to each characteristic in the chest X-ray images based on a result of the analysis of the characteristics of the pulmonary hila;
   sorting the chest X-ray images into a normal group and an un-normal group based on a result of the analysis of the characteristics of the pulmonary hila, wherein sorting the chest X-ray images includes ranking the chest X-ray images based on the total points in each chest X-ray image; and
   displaying a result of the sorting.

2. The method according to claim 1, further comprising analyzing a left-right symmetry of the lung images.

3. The method according to claim 1, further comprising analyzing characteristics of costophrenic angles in the lung images.

4. The method according to claim 1, further comprising analyzing a continuity of ribs in the lung images.

5. The method according to claim 1, further comprising analyzing a characteristic of a heart width in the lung images.

6. The method according to claim 1, further comprising analyzing a characteristic of intensity of each lung image.

7. The method according to claim 6, wherein analyzing a characteristic of intensity comprises analyzing an average intensity.

8. An image processing apparatus configured to process a plurality of chest X-ray images photographed by an X-ray imaging apparatus, said image processing apparatus comprising:
   a device configured to analyze characteristics of lung images in the plurality of chest X-ray images and apply a point to each characteristic in the chest X-ray images based on a result of the analysis of the characteristics, wherein the characteristics include a heart width and continuity of ribs;
   a device configured to sort the plurality of chest X-ray images into a normal group and an un-normal group based on a result of the analysis of the characteristics, wherein sorting the chest X-ray images includes ranking the chest X-ray images based on the total points in each chest X-ray image; and
   a device configured to display a result of the sorting.

9. The image processing apparatus according to claim 8, wherein the characteristics further comprise left-right symmetry of the lung images.

10. The image processing apparatus according to claim 8, wherein the characteristics further comprise characteristics of costophrenic angles.

11. The image processing apparatus according to claim 8, wherein the characteristics further comprise characteristics of pulmonary hila.

12. The image processing apparatus according to claim 11, wherein the characteristics of the pulmonary hila comprise size characteristics of the pulmonary hila.

13. The image processing apparatus according to claim 11, wherein the characteristics of the pulmonary hila comprise a characteristic of intensity of each pulmonary-hilum image.

14. The image processing apparatus according to claim 8, wherein the characteristics further comprise a characteristic of intensity of each lung image.

15. The image processing apparatus according to claim 14, wherein the intensity comprises an average intensity of each lung image.

* * * * *

UNITED STATES PATENT AND TRADEMARK OFFICE
CERTIFICATE OF CORRECTION

PATENT NO. : 8,433,112 B2  
APPLICATION NO. : 12/365822  
DATED : April 30, 2013  
INVENTOR(S) : Li et al.

Page 1 of 1

It is certified that error appears in the above-identified patent and that said Letters Patent is hereby corrected as shown below:

In the Specifications

In Column 5, Line 59, delete "the following coordinates" and insert -- the coordinates --, therefor.

Signed and Sealed this  
Thirteenth Day of August, 2013

Teresa Stanek Rea  
*Acting Director of the United States Patent and Trademark Office*